(12) United States Patent
Hearn et al.

(10) Patent No.: US 9,655,890 B2
(45) Date of Patent: May 23, 2017

(54) NICOTINE COMPOSITION

(71) Applicant: Kind Consumer Limited, London (GB)

(72) Inventors: Alex Hearn, London (GB); Stuart Bhimsen Lowe, Oxford (GB); Ritika Gupta, London (GB); Chris Moyses, Oxford (GB)

(73) Assignee: Kind Consumer Limited, London (GB)

( * ) Notice: Subject to any disclaimer, the term of this patent is extended or adjusted under 35 U.S.C. 154(b) by 0 days.

(21) Appl. No.: 14/423,850

(22) PCT Filed: Aug. 23, 2013

(86) PCT No.: PCT/GB2013/052231
§ 371 (c)(1),
(2) Date: Feb. 25, 2015

(87) PCT Pub. No.: WO2014/033437
PCT Pub. Date: Mar. 6, 2014

(65) Prior Publication Data
US 2015/0297580 A1 Oct. 22, 2015

(30) Foreign Application Priority Data
Aug. 28, 2012 (GB) .................. 1215273.2

(51) Int. Cl.
*A61K 31/465* (2006.01)
*A61K 31/428* (2006.01)
(Continued)

(52) U.S. Cl.
CPC ............ *A61K 31/465* (2013.01); *A24B 15/00* (2013.01); *A24B 15/16* (2013.01); *A24B 15/167* (2016.11);
(Continued)

(58) Field of Classification Search
CPC .... A61K 31/465; A61K 9/008; A61K 31/428; A61K 47/10; A24F 47/002; A24B 15/00
See application file for complete search history.

(56) References Cited

U.S. PATENT DOCUMENTS

| 6,413,496 B1 | 7/2002 | Goodman et al. |
| 2004/0002520 A1 | 1/2004 | Soderlund et al. |

(Continued)

FOREIGN PATENT DOCUMENTS

| CN | 101084801 A | 12/2007 |
| CN | 102080276 A | 6/2011 |

(Continued)

OTHER PUBLICATIONS

International Search Report and Written Opinion dated May 8, 2014 for Application No. PCT/GB2013/052231.
(Continued)

*Primary Examiner* — Aradhana Sasan
(74) *Attorney, Agent, or Firm* — Patterson & Sheridan, L.L.P.

(57) ABSTRACT

An inhalable composition comprising: nicotine or a pharmaceutically acceptable derivative or salt thereof; a propellant; a monohydric alcohol; and a glycol and/or glycol ether, characterized in that the ratio of monohydric alcohol:glycol or glycol ether by weight is from 6:1 to 1:1.

36 Claims, 4 Drawing Sheets

(51) Int. Cl.
  *A61K 47/10* (2017.01)
  *A61K 9/00* (2006.01)
  *A24B 15/00* (2006.01)
  *A24F 47/00* (2006.01)
  *A24B 15/16* (2006.01)
  *A61M 15/06* (2006.01)
  *A61M 15/00* (2006.01)
  *A61K 9/08* (2006.01)

(52) U.S. Cl.
  CPC ............ *A24F 47/002* (2013.01); *A61K 9/008* (2013.01); *A61K 31/428* (2013.01); *A61K 47/10* (2013.01); *A61K 9/08* (2013.01); *A61M 15/0093* (2014.02); *A61M 15/06* (2013.01); *A61M 2209/045* (2013.01)

(56) References Cited

U.S. PATENT DOCUMENTS

2006/0018840 A1* 1/2006 Lechuga-
  Ballesteros ............ A01N 43/40
  424/45

2010/0236562 A1  9/2010  Hearn et al.
2011/0213021 A1* 9/2011  Kandula .............. C07D 339/04
  514/440

FOREIGN PATENT DOCUMENTS

| | | |
|---|---|---|
| CN | 102266125 A | 12/2011 |
| GB | 1017032 | 1/1966 |
| JP | H04069990 B | 11/1992 |
| JP | 2005533770 A | 11/2005 |
| JP | 2010531188 A | 9/2010 |
| JP | 2010280721 A | 12/2010 |
| JP | 2012513275 A | 6/2012 |
| WO | 03/101454 | 12/2003 |
| WO | 2009/135729 | 11/2009 |
| WO | WO 2011/107737 A1 * | 9/2011 ............. A24F 47/00 |

OTHER PUBLICATIONS

United Kingdom Search Report dated Dec. 27, 2012 for Application No. GB1215273.2.
Summary (in English) of Japanese Official Action dated Feb. 28, 2017, for Japanese Patent Application No. 2015-529114.

* cited by examiner

NICOTINE COMPOSITION

The invention relates to an inhalable composition comprising nicotine, its method of manufacture and simulated cigarettes containing the inhalable composition.

The smoking of tobacco is an addictive activity associated with the pleasurable feeling caused by nicotine, and reinforced by the habits and rituals of the smoker. These attributes combine to make it very difficult to give up smoking, despite the numerous adverse health effects of the carbon monoxide, tar, and other combustion products of tobacco. It is not the nicotine itself that is harmful to health, rather the by-products of tobacco smoke.

There are a number of smoking cessation aids currently on the market, such as nicotine skin patches, nicotine-containing gums, nicotine cartridges, and nicotine inhalers. These aids attempt to achieve the increase in blood nicotine content provided by tobacco smoke without the associated dangerous by-products, but do little to address the habitual aspects of cigarette smoking. Furthermore, detailed analysis of the delivery characteristics of the above smoking cessation aids has revealed a wide variation in effects in terms of speed of delivery, concentration, persistence, and bioavailability (Hukkanen et al., *Pharmacol. Rev.* 2005, 57, 79). Accordingly, since these aids do not provide a pharmacokinetic profile similar to that of a conventional cigarette, their use in effective nicotine replacement therapy (NRT) or as an alternative to recreational smoking of conventional cigarettes is only very limited.

WO2011/095781 describes a simulated smoking device comprising a canister containing a nicotine composition, and a refillable inhaler shaped like a cigarette. GB1528391 describes a composition comprising nicotine or a nicotine salt, a solvent for the dissolution thereof, a flavourant, and a propellant.

WO2006/004646 describes an inhalable nicotine composition containing free base nicotine with an organic acid, HFA and optionally a co-solvent. However, none of these compositions provide a user with a pharmacokinetic profile similar to that of a conventional cigarette. US2009/005423 describes an application for a nicotine composition that aims to mimic the plasma-nicotine concentration generated by smoking a cigarette, namely a rapid, strong peak in concentration after application of the composition to the oral mucosa. However, the peak provided by this composition occurs on a shorter timescale and also decays away quicker than that typically observed as a result of conventional cigarette smoking.

The present invention seeks to tackle at least some of the problems associated with the prior art or at least to provide a commercially acceptable alternative solution thereto.

In a first aspect, the present invention provides an inhalable composition comprising:
- nicotine or a pharmaceutically acceptable derivative or salt thereof;
- a propellant;
- a monohydric alcohol; and
- a glycol and/or glycol ether, characterised in that the ratio of monohydric alcohol:glycol and/or glycol ether by weight is from 6:1 to 1:1.

Each aspect or embodiment as defined herein may be combined with any other aspect(s) or embodiment(s) unless clearly indicated to the contrary. In particular any feature indicated as being preferred or advantageous may be combined with any other feature or features indicated as being preferred or advantageous.

The term "diameter" as used herein encompasses the largest dimension of a droplet. Droplet diameters referred to herein may be measured using a Malvern Spraytec device.

The term "Dv10" as used herein refers to a droplet diameter that no more than 10% vol of the droplets in a composition have a smaller diameter than. The term "Dv50" as used herein refers to a droplet diameter that no more than 50% vol of the droplets in a composition have a smaller diameter than. The term "Dv90" as used herein refers to a droplet diameter that no more than 90% vol of the droplets in a composition have a smaller diameter than. Dv10, Dv50 and Dv90 values may be determined using a Malvern Spraytec device.

The term "nicotine free base" as used herein refers to the form of nicotine that predominates at high pH levels, i.e. at pH levels above 7.

The term "$C_{max}$" as used herein refers to the maximum measured concentration of a compound, in this case nicotine, in the bloodstream of a subject.

The term "$t_{max}$" as used herein refers to the time taken to achieve $C_{max}$ from administration of the compound.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

The composition of the present invention may be delivered to a user via oral inhalation. Accordingly, it is effective for use in nicotine replacement therapy (NRT) or as an alternative to recreational smoking of conventional cigarettes, since it mimics some of the habitual aspects of smoking.

In both conventional cigarettes and electronic "e"-cigarettes, nicotine must be heated in order to be delivered to a user via inhalation (to result in combustion in the case of a conventional cigarette or to result in vaporisation in the case of an e-cigarette). Such heating results in the generation of harmful by-products, such as aldehydes, ketones, nitrosamines and heavy metals, which are then also delivered to the user via inhalation. In contrast, the composition of the present invention may be delivered via inhalation without the application of heat, meaning that the levels of harmful species delivered to a user are significantly reduced. Furthermore, the absence of a heating step is advantageous since it avoids the need for a power source such as a battery (in the case of an e-cigarette) or lighting means such as matches (in the case of a conventional cigarette).

The glycol and/or glycol ether aids the dissolution of the nicotine or a pharmaceutically acceptable derivative or salt thereof in the composition. This avoids the presence of precipitates of nicotine (or other additives such as saccharin, if present) in the composition, which could cause irritation when delivered to a user. In addition, the presence of glycol or glycol ether reduces the degradation of nicotine that occurs over time, thereby increasing the long-term stability or "shelf life" of the composition. For example, chromatographic analysis of the composition according to the first aspect of the present invention, after six months' storage at 40° C., 75% relative humidity, may indicate the following impurity percentage fractions relative to nicotine fraction: anabasine at no greater than 0.3% area; anatabine at no greater than 0.3% area; β-nicotyrine at no greater than 0.3% area; cotinine at no greater than 0.3% area; myosmine at no greater than 0.3% area; nicotine n-oxide at no greater than 0.3% area; nornicotine at no greater than 0.3% area. These impurity limits lie within the European Pharmacopoeia specifications for nicotine starting material, indicating the favourable degradation characteristics of the composition over the composition lifetime. Notwithstanding this, the European Pharmacopoeia should not be taken as limiting in any way the allowable impurities tolerances claimed in this invention.

Monohydric alcohol has a lower viscosity than a glycol or glycol ether. Accordingly, the composition is able to form droplets of a smaller diameter in comparison to compositions in which the monohydric alcohol is not present. The present inventors have surprisingly found that the ratio of monohydric alcohol to glycol or glycol ether specified above results in a composition with a desired combination of both long term stability (for example the composition remains as a single phase for at least a week at a temperature of 2-40° C.) and small droplet size.

Advantageously, when a nicotine composition having such a ratio of monohydric alcohol:glycol or glycol ether is delivered to a user via a conventional pressurised metered-dose inhaler (pMDI), the composition is delivered in the form of droplets, some of which (such as, for example, at least 10% vol) have a diameter of less than 10 μm, typically less than 5 μm. Typically, the majority (such as, for example, at least 50% vol) of the droplets have a diameter of less than 5 μm, typically substantially all (such as, for example, at least 90% vol, or even at least 95% vol) of the droplets have a diameter of less than 5 μm. Advantageously, when administered to a user, droplets with a size of less than 10 μm tend to be deposited in the lungs, rather than, for example, the oropharynx. Accordingly, at least some (such as, for example, at least 10% w/w), typically substantially all (such as, for example, at least 90% w/w), of the nicotine enters the bloodstream via the pulmonary route. This means that the composition, when inhaled orally, is more able to mimic the pharmacokinetic profile of a conventional cigarette compared to nicotine compositions of the prior art. Since the composition may be administered via oral inhalation and is able to mimic the pharmacokinetic profile of a conventional cigarette, it is particularly effective for use in NRT or as an alternative to recreational smoking of conventional cigarettes.

Typically at least some (such as, for example, at least 10% vol) of the droplets have a size of from 0.5 to 3 μm. Such droplets may be deposited in the deep lung, and are therefore particularly able to enter the blood stream via the pulmonary route. Typically at least some (such as, for example, at least 10% vol) of the droplets have a diameter of from 0.4 to 0.5 μm. Such droplets are particularly able to mimic the pharmacokinetic profile of a conventional cigarette, since conventional cigarette smoke has a mean particle diameter in the range of from 0.4 to 0.5 μm.

In contrast to compositions of the prior art, the composition of the present invention is able to form small diameter droplets without the use of organic acids. Accordingly, the level of irritation experienced by a user of the compositions is reduced.

When the composition of the present invention is delivered to a user via one of the simulated cigarettes described below, the droplets may exhibit the following droplet size profile:

Dv 90 of less than 20 μm, typically less than 5 μm, more typically less than 3, even more typically less than 2.9 μm, and/or Dv 50 of less than 6 μm, typically less than 0.8 μm, more typically less than 0.7 μm, even more typically less than 0.6 μm, and/or Dv 10 of less than 2 μm, typically less than 0.3 μm, more typically less than 0.25 μm, even more typically less than 0.2 μm.

This particular droplet size profile is similar to the particle size profile of tobacco smoke. Accordingly, the pharmacokinetic profile of the delivered composition closely mimics that of a conventional cigarette. In particular, delivery of the composition to a user generates an extended peak of high nicotine concentration with a short $t_{max}$, i.e. the time from first inhalation to the maximum nicotine-plasma level. As a result, the composition is highly effective for use in nicotine replacement therapy (NRT) or as an alternative to recreational smoking of conventional cigarettes.

In summary, the composition of the first aspect of the present invention is, inter alia, stable, causes little irritation to a user, is able to mimic the pharmacokinetic profile of a conventional cigarette, may be delivered via oral inhalation and without the application of heat, and results in the delivery of less harmful species to a user in comparison to a conventional cigarette or e-cigarette.

Any suitable source of nicotine may be employed. For example, the nicotine may be nicotine free base, a nicotine derivative and/or a nicotine salt. Where a nicotine free base is employed, it may be employed in liquid form. Where a nicotine salt is employed, it may be employed in the form of a solution. Suitable nicotine salts include salts formed of the following acids: acetic, proprionic, 1,2-butyric, methylbutyric, valeric, lauric, palmitic, tartaric, citric, malic, oxalic, benzoic, alginic, hydrochloric, chloroplatinic, silicotungstic, pyruvic, glutamic and aspartic. Other nicotine salts, such as nicotine bitartrate dehydrate, may also be employed. Mixtures of two or more nicotine salts may be employed. Nicotine salts may also be in liposomal encapsulation. Such encapsulation may allow the nicotine concentration of a composition to be further increased without nicotine precipitation occurring.

As discussed above, the ratio of monohydric alcohol: glycol or glycol ether by weight results in a combination of both stability and a desired droplet size profile.

Preferably the ratio of monohydric alcohol:glycol or glycol ether by weight is from 5:1 to 1.5:1, preferably from 4:1 to 2:1, more preferably from 3:1 to 2.5:1, even more preferably about 2.8:1.

The glycol and/or glycol ether may be selected from propylene glycol, polypropylene glycol and polyethylene glycol (PEG), or combinations of two or more thereof. Suitably polyethylene glycols may have a molecular mass of less than 20,000 g/mol. An example of a suitable polyethylene glycol is PEG 400. Preferably the glycol or glycol ether is propylene glycol. Propylene glycol provides the composition with a particularly desirable droplet size profile and provides enhanced solvation of excipients and reduces degradation of excipients. Preferably the composition comprises from 0.1 to 2 w/w % propylene glycol, preferably from 0.1 to 1 w/w %, more preferably from 0.2 to 0.5% w/w, even more preferably from 0.25 to 0.4% w/w, still even more preferably about 0.34% w/w, based on the total weight of the composition.

Preferably the monohydric alcohol is ethanol. Ethanol has a particularly low viscosity in comparison to a glycol or glycol ether, and is therefore particularly effective at enabling the composition to form droplets of small diameter. In addition, ethanol is cheap, relatively non-harmful and readily available. Preferably the composition comprises from 0.5 to 1.5% w/w ethanol, preferably from 0.7 to 1.3% w/w, more preferably from 0.9 to 1% w/w, even more preferably about 0.95% w/w, based on the total weight of the composition.

Preferably the composition further comprises a human TAS2R bitter taste receptor agonist. The use of a human TAS2R bitter taste receptor agonist induces bronchodilation, resulting in a reduction in the levels of delivery-related coughing. Accordingly, a user is more able to tolerate the composition since it causes very little irritation.

The human TAS2R bitter taste receptor agonist may be a naturally occurring compound or a synthetic compound. Examples of suitable naturally-occurring compounds include Absinthin, Aloin, Amarogentin, Andrographolide, Arborescin, Arglabin, Artemorin, Camphor, Cascarillin, Cnicin, Crispolide, Ethylpyrazine, Falcarindiol, Helicin, Humulone isomers, Limonin, Noscapine Papaverine, Parthenolide, Quassin, Sinigrin, and Thiamine. Examples of suitable synthetic compounds include Acesulfame K, Benzoin, Carisoprodol, Chloroquine, Cromolyn, Dapsone, Denatonium benzoate, Dimethyl thioformamide, Diphenhydramine, Divinylsulfoxide, Famotidine, Saccharin, Sodium benzoate, and Sodium cyclamate.

Preferably the human TAS2R bitter taste receptor agonist is saccharin. Saccharin is particularly effective as a human TAS2R bitter taste receptor agonist, may be readily dissolved in the composition, is readily available and provides the composition with a desirable taste profile. Preferably the ratio of nicotine or a pharmaceutically acceptable derivative or salt thereof: saccharin by weight is from 12:1 to 5.5:1, preferably from 11:1 to 6:1, more preferably from 10:1 to 7:1, even more preferably from 9.5:1 to 8:1, even more preferably about 8.75:1. Lower levels of saccharin result in a composition with an unacceptable tolerability. Higher levels of saccharin result in an acceptable tolerability but are disfavoured since saccharin they may lead to precipitates of saccharin forming in the composition, which may cause irritation when the composition is administered to a user or blockage when the composition is incorporated into a simulated cigarette. Such ratios also provide the composition with an optimised taste profile.

The propellant may be a hydrofluorocarbon, preferably a hydrofluoroalkane, even more preferably 1,1,2,2-tetrafluoroethane (HFA-134a) or 1,1,1,2,3,3-heptafluoropropane (HFC-227). Such compounds are particularly effective as propellants and have no adverse effect on the body.

The composition may comprise at least 60% w/w propellant, preferably from 90 to 99.5% w/w, preferably from 96 to 99% w/w, more preferably from 98 to 99% w/w, based on the total weight of the composition. The propellant is preferably liquefied.

The composition may further comprise a flavour component. Nicotine has a bitter, long lasting taste which can often elicit a burning taste sensation. The use of a flavour component may mask this taste. Suitable flavour components include the flavour components typically added to tobacco products. Examples include carotenoid products, alkenols, aldehydes, esters and delta-lactone flavour constituents. Suitable carotenoid products include beta ionone, alpha ionone, beta-damascone, beta-damascenone, oxo-edulan I, oxo-edulan II, theaspirone, 4-oxo-beta-ionone, 3-oxo-alpha-ionone, dihydroactinodiolide, 4-oxoisophorone, safranal, beta-cyclocitral. Suitable alkenols include $C_4$ to $C_{10}$ alkenols, preferably $C_5$ to $C_8$ alkenols. Specific examples include: cis-2-Penten-1-ol, cis-2-Hexen-1-ol, trans-2-Hexen-1-ol, trans-2-Hexen-1-ol, cis-3-Hexen-1-ol, trans-3-Hexen-1-ol, trans-2-Hepten-1-ol, cis-3-Hepten-1-ol, trans-3-Hepten-1-ol, cis-4-Hepten-1-ol, trans-2-Octen-1-ol, cis-3-Octen-1-ol, cis-5-Octen-1-ol, 1-Octen-3-ol and 3-Octen-2-ol. Suitable aldehydes include benzaldehyde, glucose and cinnamaldehyde. Suitable esters include allyl hexanoate, benzyl acetate, bornyl acetate, butyl butyrate, ethyl butyrate, ethyl hexanoate, ethyl cinnamate, ethyl formate, ethyl heptanoate, ethyl isovalerate, ethyl lactate, ethyl nonanoate, ethyl valerate, geranyl acetate, geranyl butyrate, isobutyl acetate, isobutyl formate, isoamyl acetate, isopropyl acetate, linalyl acetate, linalyl butyrate, linalyl formate, methyl acetate, methyl anthranilate, methyl benzoate, methyl benzyl acetate, methyl butyrate, methyl cinnamate, methyl pentanoate, methyl phenyl acetate, methyl salicylate (oil of wintergreen), nonyl caprylate, octyl acetate, octyl butyrate, amyl acetate (pentyl acetate), pentyl hexanoate, pentyl pentanoate, propyl ethanoate, propyl isobutyrate, terpenyl butyrate, ethyl formate, ethyl acetate, ethyl propionate, ethyl butyrate, ethyl valerate, ethyl hexanoate, ethyl heptanoate, ethyl octanoate, ethyl nonanoate, ethyl decanoate, ethyl dodecanoate, ethyl myristate, ethyl palmitate. Suitable delta-lactone flavour constituents include delta-Hexalactone, delta-Octalactone, delta-Nonalactone, delta-Decalactone, delta-Undecalactone, delta-Dodecalactone, Massoia lactone, Jasmine lactone and 6-Pentyl-alpha-pyrone. Flavour components may serve to mask the taste of nicotine, which is unpleasant.

The flavour component is preferably menthol and/or vanillin. The presence of menthol, together with the saccharin, reduces the irritation experienced by a user. Preferably the composition comprises up to 0.1% w/w menthol, preferably from 0.01% w/w to 0.08% w/w, more preferably from 0.02% w/w to 0.06% w/w, even more preferably from 0.03% w/w to 0.05% w/w, still even more preferably about 0.04% w/w, based on the total weight of the composition.

The composition may comprise from 0.001% w/w to 0.045% w/w nicotine or a pharmaceutically acceptable derivative or salt thereof, preferably from 0.01% w/w to 0.045% w/w, more preferably from 0.015% w/w to 0.04% w/w, even more preferably from 0.02% w/w to 0.035% w/w, still even more preferably from 0.025% w/w to 0.03% w/w, most preferably about 0.028% w/w, based on the total weight of the composition. Such a composition provides similar effects to a "low strength" nicotine cigarette.

The composition may comprise from 0.04% w/w to 0.07% w/w nicotine or a pharmaceutically acceptable derivative or salt thereof, preferably from 0.045% w/w to 0.065% w/w, more preferably from 0.05% w/w to 0.06% w/w, even more preferably from 0.054% w/w to 0.058% w/w, still even more preferably about 0.056% w/w, based on the total weight of the composition. Such a composition provides similar effects to a "medium strength" nicotine cigarette.

The composition may comprise from 0.065% w/w to 0.1% w/w nicotine or a pharmaceutically acceptable derivative or salt thereof, preferably from 0.07% w/w to 0.095% w/w, more preferably from 0.075% w/w to 0.09% w/w, even more preferably from 0.08% w/w to 0.088% w/w, still even more preferably about 0.084% w/w, based on the total weight of the composition. Such a composition provides similar effects to a "high strength" nicotine cigarette.

A particularly preferred composition comprises, based on the total weight of the composition:
from 0.03 to 0.05% w/w menthol, preferably about 0.04% w/w,
from 0.25 to 0.4% w/w propylene glycol, preferably about 0.34% w/w,
from 0.9 to 1% w/w ethanol, preferably about 0.95% w/w, saccharin, and either:
  (i) from 0.025% w/w to 0.03% w/w nicotine or a pharmaceutically acceptable derivative or salt thereof, preferably about 0.028% w/w, or
  (ii) from 0.054% w/w to 0.058% w/w nicotine or a pharmaceutically acceptable derivative or salt thereof, preferably about 0.056% w/w, or
  (iii) from 0.08% w/w to 0.088% w/w nicotine or a pharmaceutically acceptable derivative or salt thereof, preferably about 0.084% w/w, the balance being HFA-134a, wherein the ratio of nicotine to saccharin by weight is from 9.5:1 to 8:1, preferably about 8.75:1. Such a composition exhibits a particularly desirable combination of the above-described advantages.

Preferably the total solvent content, i.e. the total content of monohydric alcohol and glycol and/or glycol ether, is less than 35% w/w, preferably less than 6% w/w, more preferably from 0.1% w/w to 2.5% w/w, based on the weight volume of the composition. Reducing the total solvent content of the composition reduces its viscosity, meaning it is more able to form more favourable droplet sizes.

Preferably the composition comprises less than 0.01% w/w nicotinic acid, more preferably less than 0.005% w/w, even more preferably less than 0.001% w/w nicotinic acid, based on the total weight of the composition. Most preferably, the composition comprises substantially no nicotinic acid. The presence of nicotinic acid may result in the formation of precipitates in the composition.

The compositions of the first aspect may "consist of" the components recited above. The compositions of the first aspect may "consist of" the components recited above together with any unavoidable impurities.

In a second aspect, the present invention provides a pressurised container containing the composition of the first aspect.

The pressurised container of the second aspect of the present invention may be used to release a gaseous flow of the nicotine composition of the first aspect to a user. For example, the pressurised container may be provided with means for delivering the contents of the container to the lungs of a user. Such means may take the form of a button, trigger or breath-activated mechanism. The pressurised container may be used to deliver an unmetered dose of nicotine to the user. This may be advantageous over prior art methods of NRT, such as conventional inhalers, nasal sprays, lozenges and patches currently on the market, because it can allow autonomy in nicotine replacement regulation, where there the user can regulate the amount of compositional nicotine he or she wishes to inhale. In addition, the pressurised container can be used as an alternative to recreational smoking of conventional cigarettes.

The pressurised container of the present invention may be used to release the composition to a user without the need for a separate source of energy. For example, the composition may be released without requiring the heating of substrates, combustion of material or a battery powered electric current. As discussed above, this can result in a reduction in the levels of harmful by-products delivered to a user.

The pressurised container of the present invention may take the form of a pressurised canister, for example, a pressurised aluminium canister. The canister may be fully recyclable and/or reusable. The canister may be refilled as required by a vending machine or a larger container containing the desired composition under a high pressure gradient. In one embodiment, the canister is a AW5052 aluminium canister.

The pressurised container may be a simulated cigarette.

The pressurised container may be capable of dispensing the composition as a mixture of aerosolised droplets. Preferably, the mixture has a particle size distribution that is similar to tobacco smoke. The mixture may have the appearance of a vapour or smoke.

The pressurised container may be pressurised to a pressure of from $3\times10^5$ Pa to $1.5\times10^7$ Pa, preferably from $5\times10^5$ Pa to $2\times10^6$ Pa, more preferably from $5.5\times10^5$ Pa to $1\times10^6$ Pa, even more preferably at about $6\times10^5$ Pa.

The pressurised container may be used to re-fill a simulated cigarette, in particular the simulated cigarette of the third aspect of the present invention described below.

The pressurised container contents may comprise from 16 to 18 mg nicotine, preferably about 17.18 mg nicotine; from 7 to 9 mg menthol, preferably about 8.176 mg menthol; from 1 to 3 mg saccharin, preferably about 1.963 mg saccharin; from 68 to 72 mg propylene glycol, preferably about 69.5 mg propylene glycol; from 190 to 200 mg ethanol, preferably about 194.2 mg ethanol; and from 18 to 22 g HFA-134a, preferably about 20.15 g HFA-134a. Alternatively, the pressurised container contents may comprise from 10 to 12 mg nicotine, preferably about 11.45 mg nicotine; from 7 to 9 mg menthol, preferably about 8.176 mg menthol; from 1.1 to 1.4 mg saccharin, preferably about 1.288 mg saccharin; from 68 to 72 mg propylene glycol, preferably about 69.5 mg propylene glycol; from 190 to 200 mg ethanol, preferably about 194.2 mg ethanol; from 18 to 22 g HFA-134a, preferably and about 20.16 g HFA-134a. Alternatively, the pressurised container contents may comprise from 5 to 7 mg nicotine, preferably about 5.73 mg nicotine; from 7 to 9 mg menthol, preferably about 8.176 mg menthol; from 0.5 to 0.8 mg saccharin, preferably about 0.654 mg saccharin; from 68 to 72 mg propylene glycol, preferably about 69.5 mg propylene glycol; from 190 to 200 mg ethanol, preferably about 194.2 mg ethanol; and from 18 to 22 g HFA-134a, preferably about 20.16 g HFA-134a. Alternatively, the pressurised container contents may comprise about from 7 to 9 mg menthol, preferably 8.176 mg menthol; from 0.1 to 0.3 mg saccharin, preferably about 0.204 mg saccharin; from 68 to 72 mg propylene glycol, preferably about 69.5 mg propylene glycol; from 190 to 200 mg ethanol, preferably about 194.2 mg ethanol; and from 18 to 22 g HFA-134a, preferably about 20.17 g HFA-134a.

The pressurised container may be used to re-fill a simulated cigarette. Such a "re-fill" container may comprise from 0.6 to 0.7 mg nicotine, preferably about 0.672 mg nicotine; from 0.2 to 0.4 mg menthol, preferably about 0.32 mg menthol; from 0.07 to 0.09 mg saccharin, preferably about 0.077 mg saccharin; from 2.5 to 2.9 mg propylene glycol, preferably about 2.72 mg propylene glycol; from 7 to 9 mg ethanol, preferably about 7.6 mg ethanol; and from 760 to 800 mg HFA-13a, preferably about 788.6 mg HFA-134a. Alternatively, such a re-fill may comprise from 0.4 to 0.5 mg nicotine, preferably about 0.448 mg nicotine; from 0.2 to 0.4 mg menthol, preferably about 0.32 mg menthol; from 0.04 to 0.06 mg saccharin, preferably about 0.051 mg saccharin; from 2.5 to 2.9 mg propylene glycol, preferably about 2.72 mg propylene glycol; from 7 to 9 mg ethanol, preferably about 7.6 mg ethanol; and from 760 to 800 mg HFA-134a, preferably about 788.9 mg HFA-134a. Alternatively, each refill may comprise from 0.1 to 0.3 mg nicotine, preferably about 0.224 mg nicotine, from 0.2 to 0.4 mg menthol, preferably about 0.32 mg menthol; from 0.01 to 0.03 saccharin, preferably about 0.026 mg saccharin, from 2.5 to 2.9 mg propylene glycol, preferably about 2.72 mg propylene glycol, from 7 to 9 mg ethanol, preferably about 7.6 mg ethanol, and from 760 to 800 mg HFA-134a, preferably about 789.1 mg HFA-134a. Alternatively, such a re-fill may comprise from 0.2 to 0.4 mg menthol, preferably about 0.32 mg menthol, from 0.007 mg to 0,009 mg saccharin, preferably about 0.008 mg saccharin, from 2.5 to 2.9 mg propylene glycol, preferably about 2.72 mg propylene glycol; from 7 to 9 mg ethanol, preferably about 7.6 mg ethanol; and from 760 to 800 mg HFA-134a, preferably about 789.4 mg HFA-134a.

The nicotine in the pressurised container contents described above may, of course, be substituted with a pharmaceutically acceptable derivative or salt thereof.

In a third aspect, the present invention provides a simulated cigarette device comprising:
  a housing;
  a pressurised reservoir of inhalable composition within the housing;
  an outlet for the inhalable composition from the reservoir and out of the housing, the outlet being configured to eject inhalable composition therefrom in the form of droplets, at least some of the droplets having a diameter of 10 µm or less; and
  an outlet valve for controlling the flow of inhalable composition through the outlet,
wherein the inhalable composition is according to the first aspect.

For example, the outlet may be configured to eject inhalable composition therefrom in the form of droplets, at least 1% vol of the droplets having a diameter of 10 µm or less.

Preferably the majority of the droplets (such as, for example, at least 50% vol) have a diameter of 10 µm or less, more preferably substantially all of the droplets (such as, for example, at least 90% vol) have a diameter of 10 µm or less. Preferably at least some of the droplets (such as, for example, at least 1% vol) have a diameter of 5 µm or less, preferably the majority of the droplets (such as, for example, at least 50% vol) have a diameter of 5 µm or less, more preferably substantially all of the droplets (such as, for example, at least 90% vol) have a diameter of 5 µm or less Preferably the outlet valve is a breath-activated valve.

Preferably the simulated cigarette further comprises a capillary plug extending from the vicinity of the outlet valve into the reservoir, filling at least 50% of the volume of the reservoir and being configured to wick the inhalable composition towards the outlet.

Preferably the simulated cigarette has a breath operated valve and the housing has an outlet end and an opposite end and the simulated cigarette further comprises:
  a composition flow path for the flow of the composition from the reservoir along the flow path and out of the outlet at the outlet end of the housing;
  a flexible diaphragm within the housing defining an air flow path from an air inlet to an air outlet at the outlet end of the housing;
  a valve element movable with the diaphragm and biased by a biasing force into a position in which it closes the composition flow path;
  wherein suction on the outlet end causes a flow through the air flow path providing a pressure differential over the valve element thereby lifting the valve element against the biasing force to open the composition flow path; and
  wherein the biasing force is arranged to close the composition flow path once the suction ceases.

Preferably the simulated cigarette has a breath operated valve and the breath-activated valve is a non-metered valve between the outlet and the reservoir, the breath-activated valve comprising a flow path extending from the reservoir to the outlet end, at least a portion of the flow path being a deformable tube, and a clamping member which pinches the deformable tube closed when no suction force is applied to the device and releases the tube to open the flow path when suction is applied at the outlet, to provide uninterrupted flow from the reservoir to the outlet. This simulated cigarette is referred to hereinafter as a "pinch valve" simulated cigarette.

Preferably the simulated cigarette further comprises a re-fill valve in communication with the reservoir via which the reservoir may be refilled. The simulated cigarette may be re-filled from a container according to the second aspect of the present invention.

Preferably the size of the reservoir, the pressure within the reservoir and the size of the outlet at its narrowest point are arranged so that, when the outlet valve is fully opened, the reservoir will discharge in less than 30 seconds.

Preferably the simulated cigarette is configured to eject droplets of composition therefrom in which that at least 97% vol of the droplets have a diameter of less than 10 μm, preferably at least 98% vol, more preferably at least 98.5% vol, even more preferably at least 99% vol. Droplets of diameter less than 10 μm are deposited in the lungs, meaning that a pharmacokinetic profile similar to that of a conventional cigarette is provided.

Preferably the simulated cigarette is configured to eject droplets of composition therefrom having the following size profile:

- Dv 90 of less than 20 μm, preferably less than 5 μm, more preferably less than 3 μm, even more preferably less than 2.9 μm, and/or
- Dv 50 of less than 6 μm, preferably less than 0.8 μm, more preferably less than 0.7 μm, even more preferably less than 0.6 μm, and/or
- Dv 10 of less than 2 μm, preferably less than 0.3 μm, more preferably less than 0.25 μm, even more preferably less than 0.2 μm.

Accordingly, in one embodiment, the simulated cigarette is configured to eject droplets with the following size profile: Dv 90$<$20 μm, Dv 50$<$6 μm and Dv 10$<$2 μm; preferably with the following size profile: Dv 90$<$5 μm, Dv 50$<$0.8 μm and Dv 10$<$0.3 μm; more preferably with the following size profile: Dv 90$<$3 μm, Dv 50$<$0.7 μm and Dv 10$<$0.25 μm; even more preferably with the following size profile: Dv 90$<$2.9 μm, Dv 50$<$0.6 μm and Dv 10$<$0.2 μm.

Such a size profile is similar to that of a conventional cigarette, meaning that the pharmacokinetic profile provided closely mimics that of a conventional cigarette.

The simulated cigarette may provide a user with a nicotine arterial $C_{max}$ of up to 15 ng/ml, typically from 2 to 10 ng/ml, or even from 4 to 8 ng/ml. $C_{max}$ values greater than about 2 ng/ml provide a user with a "head rush" as experienced when smoking a conventional cigarette.

The simulated cigarette may provide these $C_{max}$ values with a $t_{max}$ of from 10 seconds to 20 minutes, typically from 5 minutes to 15 minutes, often about 12 minutes. Compared to simulated cigarette devices of the prior art, such $t_{max}$ values are closer to those exhibited by conventional cigarettes. Accordingly, the present invention more closely mimics the pharmacokinetic profile of a conventional cigarette, and is therefore particularly effective for use in NRT or as an alternative to recreational smoking of conventional cigarettes.

Preferably the simulated cigarette is configured to eject composition therefrom at a rate of from 0.5 to 3 liters per minute. This rate is similar to the rate smoke is ejected from a conventional cigarette. Preferably the simulated cigarette is configured to provide an inhalation resistance of from 1 to 7 kPa, preferably about 4 kPa. This inhalation resistance is similar to that provided by a conventional cigarette. When the simulated cigarette is configured to have the above ejection rate and/or inhalation resistance, preferably the simulated cigarette is configured to deliver nicotine to a user at a rate of from 0.01 to 0.06 mg/ml. This is less than a conventional cigarette. However, since the habitual aspects of smoking have been mimicked by the above ejection rate and inhalation resistance, a user will experience the same level of satisfaction with a lower level of inhaled nicotine in comparison to conventional smoking cessation aids.

In a fourth aspect, the present invention provides a method of manufacturing the composition of the first aspect, the method comprising:

preparing a pre-mixture comprising a polyhydric alcohol and a glycol and/or glycol ether, and optionally a TAS2R taste receptor agonist and/or flavouring agent, wherein the ratio of polyhydric alcohol:glycol or glycol ether by weight is from 6:1 to 1:1;

adding nicotine or a pharmaceutically acceptable derivative or salt thereof to the pre-mixture to obtain a nicotine-containing mixture; and adding a propellant to the nicotine-containing mixture.

If the nicotine is added before the polyhydric alcohol and glycol or glycol ether are combined, then precipitation of nicotine may occur. Likewise, if the composition comprises other components, such as a flavouring component or a TAS2R taste receptor agonist, then these components should be fully mixed into the pre-mixture before the nicotine is added in order to avoid precipitation of nicotine. In particular, it has been found that when the composition comprises menthol, the menthol should be fully dissolved into the pre-mixture before the nicotine is added in order to avoid precipitation of nicotine.

When the composition is to include a TAS2R taste receptor agonist and/or a flavouring component, preferably the polyhydric alcohol and glycol or glycol ether are combined before the TAS2R taste receptor agonist and/or a flavouring component are added. This avoids precipitation of the flavouring component or TAS2R taste receptor agonist.

In a fifth aspect the present invention provides a composition comprising:

nicotine or a pharmaceutically acceptable derivative or salt thereof;

a monohydric alcohol; and a glycol and/or glycol ether, characterised in that the ratio of monohydric alcohol:glycol or glycol ether by weight is from 6:1 to 1:1.

Such a composition may be used as an intermediate in the manufacture of the composition of the first aspect. The preferred additional components, concentrations and ratios of the first aspect are also preferred in the third aspect.

In a sixth aspect, the present invention provides a simulated cigarette configured to provide a user thereof with a nicotine venous $C_{max}$ of up to 15 ng/ml and/or with a $t_{max}$ of from 10 seconds to 20 minutes.

In a seventh aspect, the present invention provides a method of treating a condition selected from: nicotine addiction and neurodegenerative diseases such as Alzheimer's and Parkinson's using the composition of the first aspect of the present invention.

Embodiments of the first aspect of present invention may exhibit the following advantages over the prior art. The identity and relative concentrations of the solvents in the composition are optimised to provide enhanced long-term stability (characterised by, for example, absence of precipitates, lack of phase separation, negligible formation of by-products, lower incidence of impurities), and further the identity and relative concentrations of the volatile and non-volatile solvents in the composition are optimised such that the aerosol generated via a suitable delivery method is deposited in the lungs (characterised by, for example, optimised droplet/particle size distribution), so that the nicotine contained therein enters the bloodstream via the pulmonary route. Furthermore, the concentration of flavorants and TAS2R bitter taste agonists in the composition may be optimised to enhance palatability and tolerability (characterised by, for example, lower incidence of adverse events such as cough and respiratory tract/throat irritation, which may inhibit effective delivery of the composition to the lungs) such that the user will be inclined to repeatedly administer the composition in the manner of a cigarette smoker. Yet further, the composition may be delivered to a user via a simulated cigarette device that effectively mimics the 'feel' of smoking. Still further, the method of manufacture and order of reagent addition is optimised such that nicotine, TAS2R bitter taste agonists, and/or flavourants can all be incorporated at desired levels, avoiding the formation of precipitates. Even further, the composition can be administered in such a way that clinical outcomes (characterised by, for example, favourable cravings scores and $t_{max}$ similar to that of cigarettes) can be achieved with a lower delivered dose of nicotine than has previously been possible, with a dosing regimen that feels familiar to a smoker, thereby improving the user experience and making the composition more effective as an alternative to combustible tobacco products. A further advantage may be realised when using the composition as a treatment for medical conditions.

The present invention is described by way of example in relation to the following non-limiting figures.

EXAMPLES

Figure 1:
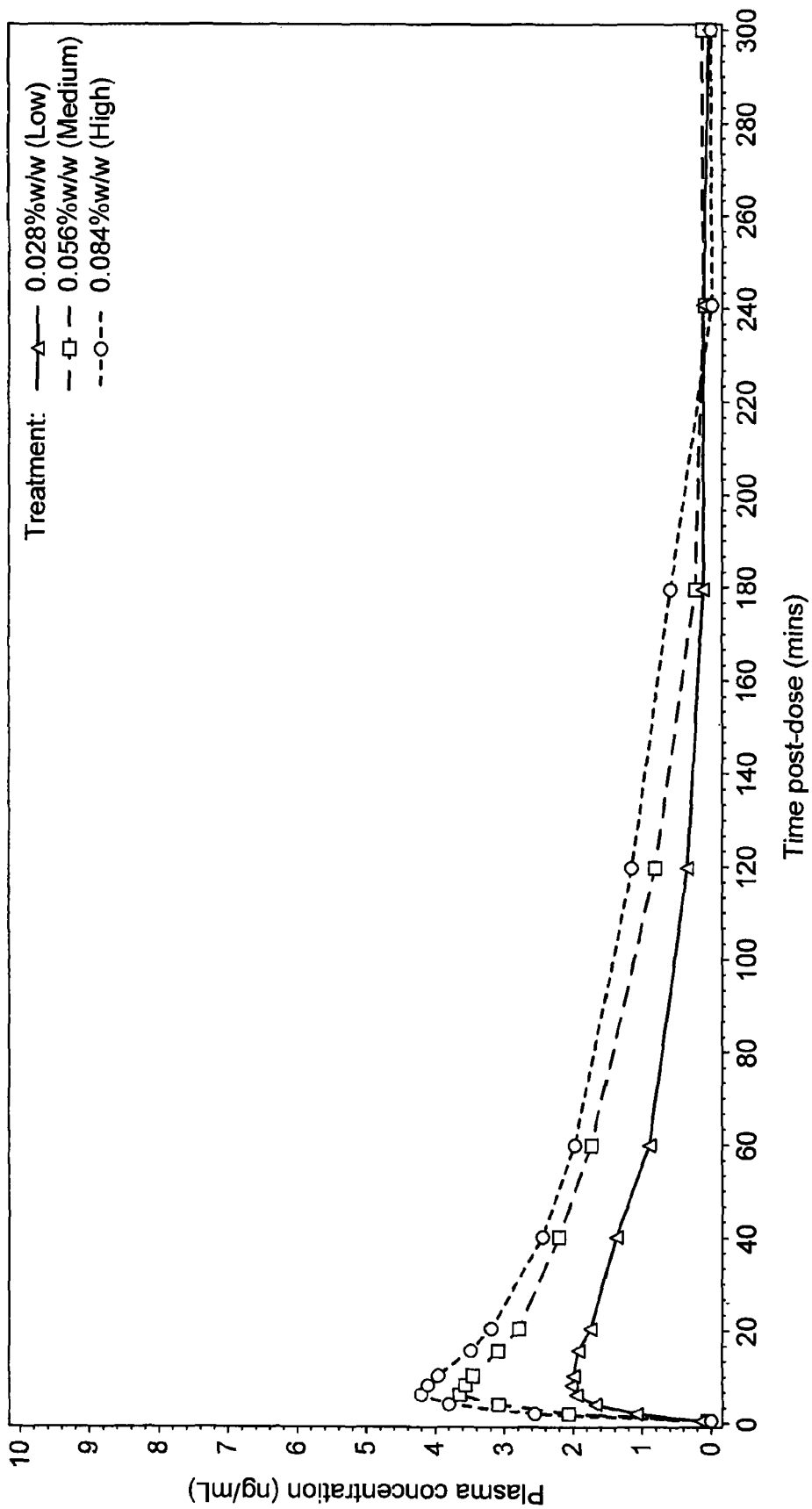
FIG. 1 shows a graph of mean arterial plasma concentrations of nicotine over time for subjects administered the "high", "medium" or "low" strength nicotine compositions of the first aspect of the present invention.

The invention will now be described with reference to the following non-limiting examples.

Method of Manufacture

The following starting materials were used:
Saccharin (Ph. Eur)
Propylene glycol (EP grade)
Menthol (Ph Eur.)
Ethanol (100% BP, Ph. Eur.)
Nicotine (Ph. Eur)
HFA-134a (CPMP 1994)

Starting materials were added to a mixing vessel in the following order: (i) 5.14 g saccharin, (ii) 227.0 g propylene glycol, (iii) 32.5 g menthol and (iv) 774.0 g ethanol. The mixture was then stirred at 600 rpm for 15 minutes until the menthol pellets had fully dissolved and a clear liquid was observed. 45.6 g of nicotine was then added to the mixture and stirring was continued at 600 rpm for a further 10 minutes. The resultant mixture was then added to a pressure vessel which had been purged with HFA 134a. The vessel was then sealed before being cooled until the internal temperature reached 8-12° C., at which point the temperature was maintained. Approximately 40 kg of HFA-134a was then released into the vessel before magnetic stirring at 210 rpm commenced. HFA continued to be released into the vessel until a total of 80 kg had been added, at which point the composition was stirred at 210 rpm for a further 110 minutes. During the further stirring, the pressure was controlled to ensure that it did not exceed 4.5 bar and that the final pressure was between 3-4 bar. After stirring, the composition was dispensed into canisters.

Varying the method by adding nicotine either before the saccharin had been added or before the menthol had fully dissolved resulted in precipitation of the nicotine.

Stability

A number of compositions were prepared with varying ratios of ethanol:propylene glycol. The stability of the compositions under various conditions was determined visually, and the results are set out in Tables 1 and 2. Compositions with ethanol:propylene glycol ratios less than 1:1 separated into two phases within a week.

TABLE 1

Stability data for various ethanol:propylene glycol ratios. (Samples 1 and 2 are comparative examples).

| Excipient | Composition, %, w/w | | | | | |
|---|---|---|---|---|---|---|
| | Sample 1 | Sample 2 | Sample 3 | Sample 4 | Sample 5 | Sample 6 |
| Nicotine | 0.0840 | 0.0840 | 0.0840 | 0.0840 | 0.0840 | 0.0840 |
| Propylene glycol | 1.7000 | 1.2750 | 0.8500 | 0.5100 | 0.3400 | 0.1700 |
| Ethanol | 0.9500 | 0.9500 | 0.9500 | 0.9500 | 0.9500 | 0.9500 |
| Saccharin | 0.0096 | 0.0096 | 0.0096 | 0.0096 | 0.0096 | 0.0096 |
| Menthol | 0.0400 | 0.0400 | 0.0400 | 0.0400 | 0.0400 | 0.0400 |
| HFA 134a | 97.2164 | 97.6414 | 98.0664 | 98.4064 | 98.5764 | 98.7464 |
| Total | 100.0000 | 100.0000 | 100.0000 | 100.0000 | 100.0000 | 100.0000 |
| Ethanol:Propylene glycol | 0.56:1 | 0.75:1 | 1.12:1 | 1.86:1 | 2.79:1 | 5.59:1 |
| Visual appearance at t = 0 | X | ✓ | ✓ | ✓ | ✓ | ✓ |
| Visual appearance at t = 1 week 2-8° C. | X | X | ✓ | ✓ | ✓ | ✓ |
| Visual appearance at t = 1 week 25° C. | X | X | ✓ | ✓ | ✓ | ✓ |
| Visual appearance at t = 1 week 40° C. | X | X | ✓ | ✓ | ✓ | ✓ |
| Visual appearance at t = 2 week 2-8° C. | X | X | X | ✓ | ✓ | ✓ |
| Visual appearance at t = 2 week 25° C. | X | X | ✓ | ✓ | ✓ | ✓ |
| Visual appearance at t = 2 week 40° C. | X | X | ✓ | ✓ | ✓ | ✓ |

✓—single phase,
X—2 phases.

TABLE 2

Stability data for various ethanol:propylene glycol ratios. The term "soluble" indicates that no precipitates were observed.

| Excipient | Composition, %, w/w | | | | | | | | | |
|---|---|---|---|---|---|---|---|---|---|---|
| | Sample 7 | Sample 8 | Sample 9 | Sample 10 | Sample 11 | Sample 12 | Sample 13 | Sample 14 | Sample 15 | Sample 16 |
| Nicotine | — | — | — | — | 0.0560 | 0.0560 | 0.0560 | 0.0560 | 0.0560 | 0.0560 |
| Propylene glycol | 0.8000 | 0.8250 | 0.8500 | 0.8750 | 0.8000 | 0.8250 | 0.8500 | 0.8750 | 0.8500 | 0.4250 |
| Ethanol | 0.9500 | 0.9500 | 0.9500 | 0.9500 | 0.9500 | 0.9500 | 0.9500 | 0.9500 | 0.9500 | 0.9500 |
| Menthol | 0.0050 | 0.0050 | 0.0050 | 0.0050 | 0.0050 | 0.0050 | 0.0050 | 0.0050 | 0.0500 | 0.0500 |
| Saccharin | 0.0400 | 0.0400 | 0.0400 | 0.0400 | 0.0400 | 0.0400 | 0.0400 | 0.0400 | 0.0058 | 0.0058 |
| HFA 134a | 98.1600 | 98.1350 | 98.1100 | 98.0850 | 98.1040 | 98.0790 | 98.0540 | 98.0290 | 98.0882 | 98.5132 |
| Total | 100.0000 | 100.0000 | 100.0000 | 100.0000 | 100.0000 | 100.0000 | 100.0000 | 100.0000 | 100.0000 | 100.0000 |
| Eth:PG | 1.19 | 1.15 | 1.12 | 1.09 | 1.19 | 1.15 | 1.12 | 1.09 | 1.12 | 2.24 |
| Appearance | Soluble | Soluble | Soluble | Soluble | Soluble | Soluble | Soluble | Soluble | Soluble | Soluble |

Droplet Size Profile

The following composition was prepared:
0.04% w/w menthol,
0.006% w/w saccharin,
0.34% w/w propylene glycol,
0.95% w/w ethanol,
0.056% w/w nicotine, and
remainder HFA-134a.

The composition was inserted into nine pinch valve simulated cigarettes. Five doses were emitted from each device and the droplet size profile of each was measured using a Malvern Spraytec device. The results are set out in Table 3 below:

TABLE 3

Droplet size profile.

|  | MEAN | SD |
|---|---|---|
| Dv 10 (μm) | 0.198758 | 0.010005 |
| Dv 50 (μm) | 0.606342 | 0.094779 |
| Dv 90 (μm) | 2.806378 | 1.063722 |
| % vol <10 μm | 99.02222 | 0.77704 |

Impurities

The following composition was prepared:
0.04% w/w menthol,
0.0032% w/w saccharin,
0.34% w/w propylene glycol and
0.95% w/w ethanol,
0.028% w/w nicotine,
remainder HFA-134a.

The composition was then inserted into a pressurised container. The percentage volume of impurities with respect to nicotine concentration was assessed chromatographically at both the time of fill and after six months. The results are set out in Table 4 below:

TABLE 4

Stability data (inverted, 40° C./75% RH). N = 1, 2 and 3 refer to different pressurised containers from the same batch of composition.

|  |  | T = 6 months | | |
|---|---|---|---|---|
| Impurity | Initial | N = 1 | N = 2 | N = 3 |
| Anatabine | 0.02% | 0.1% | 0.1% | 0.1% |
| β-nicotyrine | Not detected | 0.2% | 0.2% | 0.2% |
| Cotinine | Not detected | 0.2% | 0.2% | 0.2% |
| Myosmine | 0.02% | 0.2% | 0.2% | 0.2% |
| Nicotine-n-oxide | Not detected | 0.3% | 0.3% | 0.3% |
| Nornicotine | Not detected | 0.1% | 0.1% | 0.1% |
| Anabasine | Not detected | Not detected | Not detected | Not detected |

Clinical Study

This was a three-part study to determine the safety, tolerability and pharmacokinetics of orally inhaled nicotine via the Pinch valve simulated cigarette, which contained compositions according to the first aspect of the present invention.

The following compositions were studied:
(1) "High" nicotine: 0.04% w/w menthol, 0.0096% w/w saccharin, 0.34% w/w, propylene glycol, 0.95% w/w ethanol, 0.084% w/w nicotine and 98.5764% w/w HFA-134a.
(2) "Medium" nicotine: 0.04% w/w menthol, 0.0063% w/w saccharin, 0.34% w/w propylene glycol, 0.95% w/w ethanol, 0.056% w/w nicotine and 98.6077 HFA-134a.
(3) "Low" nicotine: 0.04% w/w menthol, 0.0032% w/w saccharin, 0.34% w/w propylene glycol, 0.95% w/w ethanol, 0.028% w/w nicotine and 98.6388% w/w HFA-134a.

Part A was to assess the safety, tolerability and arterial pharmacokinetics of a single dose of orally inhaled nicotine composition via the Pinch valve simulated cigarette at the three dose levels. Part B was to assess the venous pharmacokinetics of a single dose of orally inhaled nicotine via the Pinch valve simulated cigarette. Part C was to assess the safety, tolerability and pharmacokinetics of repeat doses of orally inhaled nicotine via the Pinch valve simulated cigarette.

This study was performed on male and female participants who had smoked at least ten manufactured cigarettes per day for the last year. The study was conducted in one centre in Perth, Australia, and was performed in healthy volunteers.

Screening evaluations were conducted up to six weeks prior to anticipated study dosing and eligible participants enrolled in the study were re-assessed for continued study appropriateness prior to planned study dosing on Day −1. Any enrolled participants who were discontinued prior to study dosing were replaced.

A minimum of sixty (60) healthy volunteers were planned for enrolment over the three parts of the study. Participants were not able to participate in more than one part of the study.

Part A: This was a single blind, randomised, multi dose-level study to evaluate the tolerability and arterial pharmacokinetics of orally inhaled nicotine via the Pinch valve simulated cigarette at three doses of nicotine 0.028% w/w (low), 0.056% w/w (medium) and 0.084% w/w (high). Arterial blood sampling was required for this part of the study to investigate the rapidity of delivery to the systemic circulation. Eighteen (18) participants were enrolled into treatment group A, and were randomised to receive 2 of 3 dose levels via the Pinch valve simulated cigarette on a single study day. The nicotine dose levels were 0.028% w/w (low), 0.056% w/w (medium) and 0.084% w/w (high).

The eighteen (18) participants were randomized into three groups with each containing six participants. One group received the low nicotine dose followed by the medium nicotine dose; one group received the low nicotine dose followed by the high nicotine dose; and one group received the medium nicotine dose followed by the high nicotine dose. The first dosing took place at approximately 8 am, and the second at approximately 1.30 pm. This was to ensure that circulating nicotine concentrations from the first dose had reached baseline levels through excretion before the second dose was inhaled. Participants were blinded to the dose level of the orally inhaled nicotine via Pinch valve simulated cigarette they were to be receiving.

At the end of Part A, the pharmacokinetics, safety and tolerability data obtained from Part A were reviewed to determine which two of the three dose levels studied were to be used in Part B.

Part B: This was an open label/single blind, randomised, 3-way crossover study to evaluate the venous pharmacokinetics of two dose levels of orally inhaled nicotine via the Pinch valve simulated cigarette. Participants were blinded to the nicotine dose level of the Pinch valve simulated cigarette they received.

Twenty four (24) participants were enrolled into treatment group B. Each participant attended the clinical trial unit confined for three consecutive days to receive one complete refill of Pinch valve simulated cigarette at one nicotine dose level on one day, one complete refill of Pinch valve simulated cigarette at a second nicotine dose level on a second day and one treatment of a conventional nicotine Inhaler (10 mg) on a third day. The order in which treatment was to be received was randomised.

At the end of Part B, the pharmacokinetics, safety and tolerability data obtained from Parts A and B were reviewed to determine which one of the two dose levels studied was to be used in Part C.

Part C: This was an open label study to evaluate the tolerability and venous pharmacokinetics of repeat doses of orally inhaled nicotine via the Pinch valve simulated cigarette at one dose level of nicotine.

Eighteen (18) participants were enrolled into treatment group C. Each participant received repeat doses of nicotine over the period of one day. All participants received the same dose of nicotine via the Pinch valve simulated cigarette. One complete refill of Pinch valve simulated cigarette was inhaled every hour for 12 hours. The first dosing took place at approximately 8 am.

Study Population:

TABLE 5

Study population.

| Parameter | Statistic | Part A (N = 18) | Part B (N = 24) | Part C (N = 18) |
|---|---|---|---|---|
| Gender | | | | |
| Male | n (%) | 10 | 14 | 13 |
| Female | n (%) | 8 | 10 | 5 |
| Age (Years) | N | 18 | 24 | 18 |
| | Mean | 33.7 | 28.6 | 32.7 |
| | SD | 9.2 | 7.9 | 9.1 |
| | Median | 35.0 | 26.0 | 32.0 |
| | Min | 21 | 21 | 21 |
| | Max | 53 | 53 | 52 |
| Race | | | | |
| Asian | n (%) | 1 | 3 | 2 |
| Caucasian | n (%) | 17 | 20 | 16 |
| Other: Mixed race | n (%) | | 1 | |

Pharmacokinetic Data:

Pharmacokinetic data are illustrated in FIG. 1 and are listed in Table 6. From FIG. 1 it can be seen that the arterial sampling times were sufficient to clearly define the pharmacokinetic profile and in particular to define the plasma nicotine $C_{max}$. All timings are taken from the start of inhalation which took approximately 2 minutes to complete. The first sampling time point at +2 minutes already reveals uptake of nicotine into arterial blood. For example for the 0.056% w/w strength the mean arterial nicotine concentration had risen from zero pre-dose to 2.06 ng/ml at 2 minutes, i.e. already at more than half the eventual $C_{max}$. From this it can be inferred that plasma nicotine was rising rapidly during the process of inhalation. The mean maximum nicotine concentrations were 2.11, 3.73 and 4.38 ng/ml at the low, medium and high strengths respectively and the corresponding $t_{max}$ were 10.2, 7.3 and 6.5 minutes after the start of inhalation.

The generation of arterial pharmacokinetic data is not without some technical difficulties in terms of vascular access but in this part of the study the arterial data is valuable in demonstrating the rapidity with which nicotine reaches the arterial circulation. Since the composition is inhaled orally, one conclusion that follows is that this speed of nicotine delivery indicates that there is a degree of pulmonary delivery since oromucosal delivery, such as that provided by a conventional nicotine inhalator, is very much slower.

TABLE 6

Pharmacokinetic data (arterial concentration). $AUC_{all}$ refers to "area under the curve".

| Treatment | $C_{max}$ (ng/mL) | | $t_{max}$ (min) | | $AUC_{all}$ (min * ng/ml) | |
|---|---|---|---|---|---|---|
| | Mean | Std Dev | Mean | Std Dev | Mean | Std Dev |
| 0.028% w/w nicotine (low) | 2.113 | 0.671 | 10.2 | 3.9 | 145.7 | 132.5 |
| 0.056% w/w nicotine (medium) | 3.733 | 1.131 | 7.3 | 1.6 | 274.4 | 146.5 |
| 0.084% w/w nicotine (high) | 4.380 | 1.186 | 6.5 | 1.9 | 334.4 | 124.2 |

Figure 2:
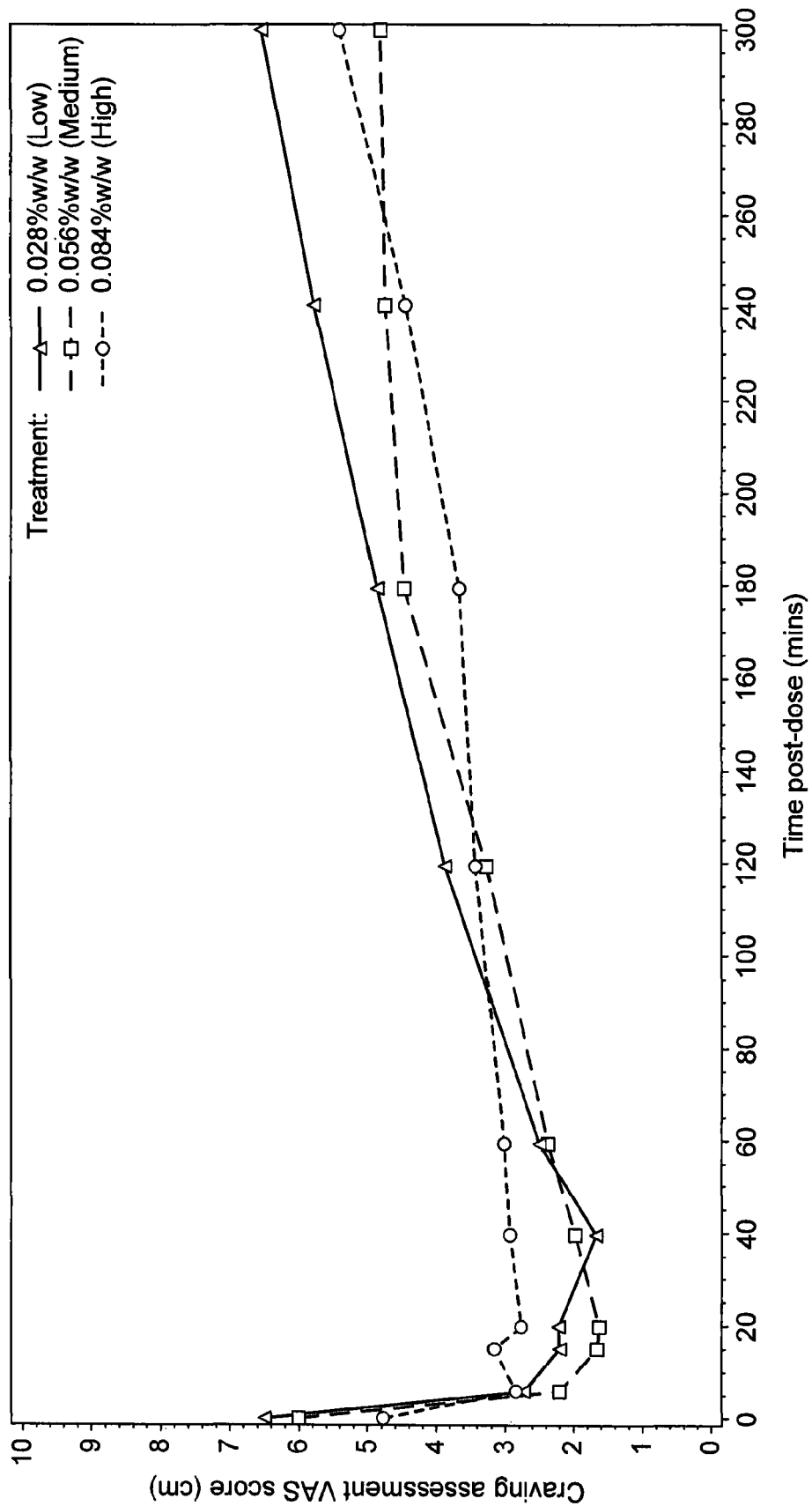
FIG. 2 shows a graph of mean craving VAS score over time for subjects administered the "high", "medium" or "low" strength nicotine compositions of the first aspect of the present invention.

Pharmacodynamic Data:

The Pharmacodynamic measurements included in all four parts of the study are repeated assessments of craving using a visual analogue scale (VAS) and the Brief Questionnaire of Smoking Urges (QSU-B). The pharmacodynamic data based on VAS are shown in FIG. 2.

The inhalation of a nicotine aerosol from the pinch valve simulated cigarette has a clear effect of reducing craving, which is apparent in all four parts of the study. In Part A, craving fell rapidly on inhalation and then gradually returned towards baseline over the next 5 hours. No statistical testing was performed on part A but the pattern of response is consistent across all 3 nicotine dose strengths.

It is notable that there was not a clear dose response relationship for craving in Part A and this perhaps reflects the importance of the hand to mouth ritual of smoking and the throat catch as well as the pharmacological effect of the rise in circulating nicotine concentrations. The QSU-B showed a consistent pattern to the craving VAS with component and total scores at their lowest 40 minutes post-dose for the low dose (0.028% w/w), and 20 minutes post-dose for the medium (0.056% w/w) and high (0.084% w/w) doses. This suggests that although the low dose has a positive effect on smoking urges, it takes longer to do so than the medium and high doses.

Figure 3:
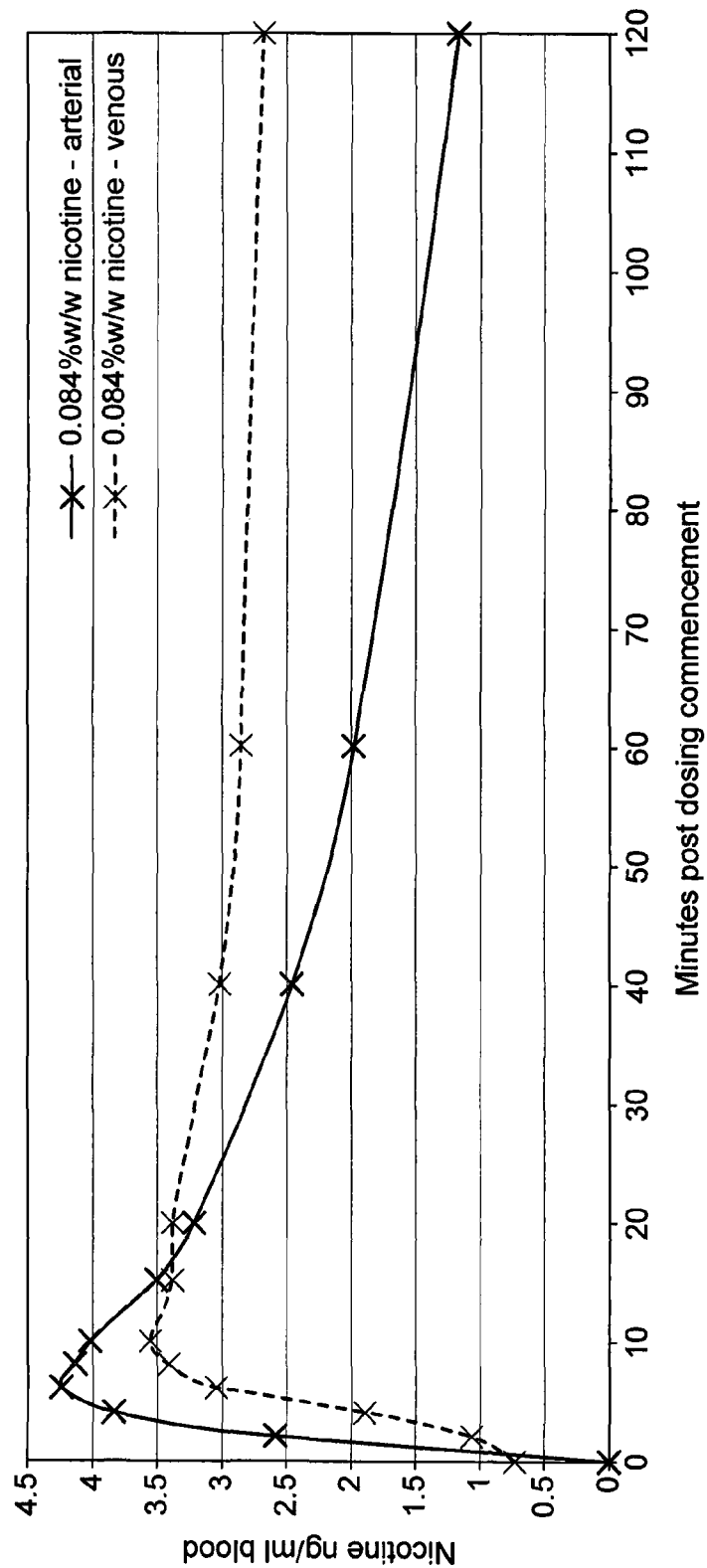
FIG. 3 shows plots of arterial and venous nicotine concentrations measured at intervals after inhalation of a "high" strength nicotine composition of the first aspect of the present invention.
Figure 4:
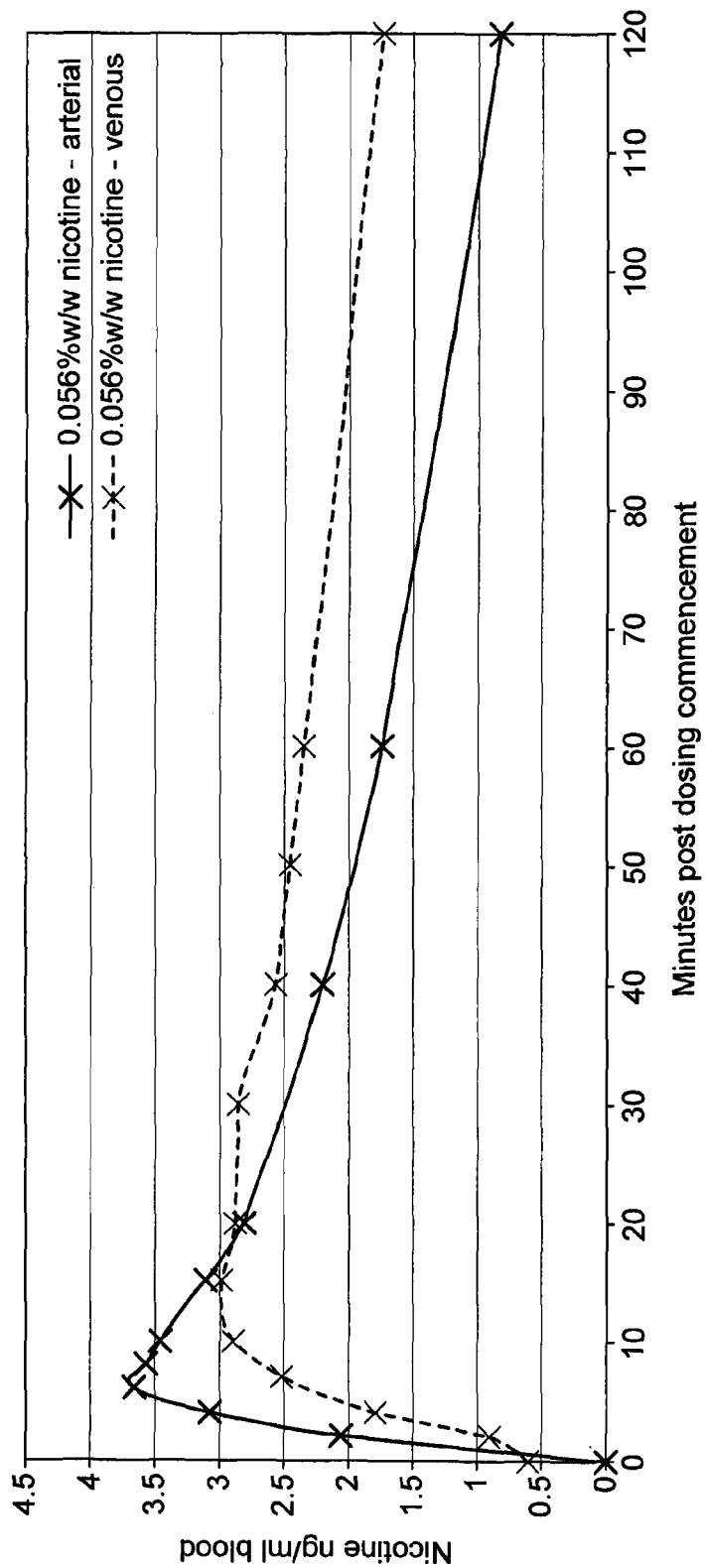
FIG. 4 shows plots of arterial and venous nicotine concentrations measured at intervals after inhalation of a "medium" strength nicotine composition of the first aspect of the present invention.

Arterial vs Venous Plots:

FIGS. 3 and 4 show plots of arterial and venous nicotine concentrations experienced by users of the "high" strength and "medium" strength compositions. These plots indicate the speed at which nicotine reaches the arterial circulation. Since the composition is inhaled orally, the speed of nicotine delivery is consistent with a degree of pulmonary delivery. Oromucosal delivery, such as that provided by commercially-available inhalers, is very much slower.

Tolerability

All adverse events were categorized as mild or moderate, there were no adverse events reported as severe. There were no significant adverse events (AE) or deaths throughout the study, and no participants discontinued treatment due to an AE.

Paraesthesia oral was by far the most frequently reported treatment-emergent adverse event (TEAE) that was reported in all parts of the study, with an overall of 40 participants (68%) reporting paraesthesia oral at least once. Seventeen (17) of the 59 participants (29%) reported throat irritation, 9 participants (15%) reported headache, 8 participants (14%) reported hypoaesthesia oral, and 6 participants (10%)

reported dizziness as a related TEAE. The remaining TEAEs occurred in less than 10% of the overall patient population.

A summary of the results is set out in Table 7 below.

TABLE 7

Adverse events logged

| Adverse Event | Part A Total (N = 18) | Part B Total (N = 23) | Part C Total (N = 18) | Study Total (N = 59) |
|---|---|---|---|---|
| Paraesthesia oral | 12 | 14 | 14 | 40 |
| Throat irritation | 3 | 8 | 6 | 17 |
| Headache | 3 | 1 | 5 | 9 |
| Hypoaesthesia oral | 2 | 4 | 2 | 8 |
| Dizziness | 3 | 2 | 1 | 6 |
| Oral discomfort | 2 | 1 | 2 | 5 |
| Dry throat | 3 | | | 3 |
| Glossodynia | 1 | 1 | 1 | 3 |
| Lip pain | 1 | 2 | | 3 |
| Nausea | 1 | | 2 | 3 |
| Chest discomfort | | 1 | 2 | 3 |
| Cough | 3 | | | 3 |

The foregoing detailed description has been provided by way of explanation and illustration, and is not intended to limit the scope of the appended claims. Many variations in the presently preferred embodiments illustrated herein will be apparent to one of ordinary skill in the art, and remain within the scope of the appended claims and their equivalents.

The invention claimed is:

1. An inhalable composition comprising:
nicotine or a pharmaceutically acceptable derivative or salt thereof;
at least 90% w/w of a propellant, wherein the propellant is a hydrofluorocarbon;
a monohydric alcohol; and
0.1 to 1% w/w of a glycol and/or glycol ether, wherein the glycol and/or glycol ether comprises propylene glycol, wherein the ratio of monohydric alcohol:glycol or glycol ether by weight is from 3:1 to 1:1, and wherein the composition is deliverable to a user using a simulated cigarette having a non-metered valve with an inhalable droplet diameter wherein at least 50 percent of the droplets have a diameter of 5 µm or less.

2. The composition of claim 1, wherein the glycol and/or glycol ether further comprises at least one of: polypropylene glycol and polyethylene glycol (PEG).

3. The composition of claim 1, wherein the monohydric alcohol is ethanol.

4. The composition of claim 3, wherein the composition comprises from 0.5 to 1.5% w/w ethanol, based on the total weight of the composition.

5. The composition of claim 1, wherein the composition further comprises a human TAS2R bitter taste receptor agonist.

6. The composition of claim 1, wherein the composition further comprises saccharin and wherein the ratio of nicotine or a pharmaceutically acceptable derivative or salt thereof:saccharin by weight is from 12:1 to 5.5:1.

7. The composition of claim 1, wherein when the composition is delivered to a user using a conventional metered dose inhaler the composition forms an inhalable droplet diameter wherein at least 50 percent of the droplets have a diameter smaller than 5 µm.

8. The composition of claim 1, wherein when the composition is delivered to a user using a conventional metered dose inhaler the composition forms an inhalable droplet diameter wherein at least 90 percent of the droplets have a diameter smaller than 5 µm.

9. The composition of claim 1, further comprising a flavour component.

10. The composition of claim 9, wherein the flavour component is menthol and the composition comprises up to 0.1% w/w menthol, based on the total weight of the composition.

11. The composition of claim 1, comprising from 0.001% w/w to 0.045% w/w nicotine or a pharmaceutically acceptable derivative or salt thereof, based on the total weight of the composition.

12. The composition of claim 1, comprising from 0.04% w/w to 0.07% w/w nicotine or a pharmaceutically acceptable derivative or salt thereof, based on the total weight of the composition.

13. The composition of claim 1, comprising from 0.065% w/w to 0.1% w/w nicotine or a pharmaceutically acceptable derivative or salt thereof, based on the total weight of the composition.

14. The composition of claim 1, comprising, based on the total weight of the composition:
from 0.03 to 0.05% w/w menthol,
from 0.25 to 0.4% w/w propylene glycol,
from 0.9 to 1% w/w ethanol,
saccharin, and
either:
(i) from 0.025% w/w to 0.03% w/w nicotine or a pharmaceutically acceptable derivative or salt thereof, or
(ii) from 0.054% w/w to 0.058% w/w nicotine or a pharmaceutically acceptable derivative or salt thereof, or
(iii) from 0.08% w/w to 0.088% w/w nicotine or a pharmaceutically acceptable derivative or salt thereof,
the balance being hydrofluoroalkane, wherein the ratio of nicotine or a pharmaceutically acceptable derivative or salt thereof to saccharin is from 9.5:1 to 8:1% w/w.

15. A pressurised container containing the composition of claim 1.

16. The pressurised container of claim 15 pressurised to a pressure of from $3 \times 10^5$ Pa to $1.5 \times 10^7$ Pa.

17. A simulated cigarette comprising:
a housing;
a pressurised reservoir of inhalable composition within the housing;
an outlet for the inhalable composition from the reservoir and out of the housing, the outlet being configured to eject inhalable composition therefrom in the form of droplets, at least some of the droplets having a diameter of 10 µm or less; and
an outlet valve for controlling the flow of inhalable composition through the outlet, wherein the inhalable composition is according to claim 1.

18. The simulated cigarette of claim 17, wherein the outlet valve is a breath-activated valve.

19. The simulated cigarette of claim 17, further comprising a capillary plug extending from the vicinity of the outlet valve into the reservoir, filling at least 50% of the volume of the reservoir and being configured to wick the inhalable composition towards the outlet.

20. The simulated cigarette of claim 18, wherein the housing has an outlet end and an opposite end and wherein the simulated cigarette further comprises:

a composition flow path for the flow of the composition from the reservoir along the flow path and out of the outlet at the outlet end of the housing;

a flexible diaphragm within the housing defining an air flow path from an air inlet to an air outlet at the outlet end of the housing;

a valve element movable with the diaphragm and biased by a biasing force into a position in which it closes the composition flow path;

wherein suction on the outlet end causes a flow through the air flow path providing a pressure differential over the valve element thereby lifting the valve element against the biasing force to open the composition flow path; and wherein the biasing force is arranged to close the composition flow path once the suction ceases.

21. The simulated cigarette according to claim 18, wherein the breath-activated valve is a non-metered valve between the outlet and the reservoir, the breath-activated valve comprising a flow path extending from the reservoir to the outlet end, at least a portion of the flow path being a deformable tube, and a clamping member which pinches the deformable tube closed when no suction force is applied to the device and releases the tube to open the flow path when suction is applied at the outlet, to provide uninterrupted flow from the reservoir to the outlet.

22. The simulated cigarette according to claim 17, further comprising a refill valve in communication with the reservoir via which the reservoir may be refilled.

23. The simulated cigarette according to claim 17, wherein the size of the reservoir, the pressure within the reservoir and the size of the outlet at its narrowest point are arranged so that, when the outlet valve is fully opened, the reservoir will discharge in less than 30 seconds.

24. The simulated cigarette according to claim 17, configured to eject droplets of composition therefrom in which at least 99% vol of the droplets have a diameter of less than 10 μm.

25. The simulated cigarette according to claim 17, configured to eject droplets of composition therefrom having the following size profile:
Dv 90 of less than 20 μm, and/or
Dv 50 of less than 5 μm, and/or
Dv 10 of less than 2 μm.

26. The simulated cigarette according to claim 17, configured to provide a user thereof with a nicotine arterial $C_{max}$ of up to 15 ng/ml and/or with a $t_{max}$ of from 10 seconds to 20 minutes.

27. The simulated cigarette according to claim 17, configured to eject composition therefrom at a rate of from 0.5 to 3 liters per minute.

28. The simulated cigarette according to claim 17, configured to provide an inhalation resistance of from 1 to 7 kPa.

29. The simulated cigarette according to claim 17, configured to deliver nicotine to a user at a rate of from 0.01 to 0.06 mg/ml.

30. A method of manufacturing the composition of claim 1, the method comprising:
preparing a pre-mixture comprising a polyhydric alcohol and a glycol or glycol ether, and optionally a TAS2R taste receptor agonist and/or flavouring component, wherein the ratio of polyhydric alcohol:glycol or glycol ether by weight is from 3:1 to 1:1;

adding nicotine or a pharmaceutically acceptable derivative or salt thereof to the pre-mixture to obtain a nicotine-containing mixture; and adding a propellant to the nicotine-containing mixture.

31. A method according to claim 30, wherein the composition comprises a TAS2R taste receptor agonist and/or flavouring component, and wherein the polyhydric alcohol and glycol or glycol ether are combined before the TAS2R taste receptor agonist and/or flavouring component are added.

32. A composition comprising:
nicotine or a pharmaceutically acceptable derivative or salt thereof;

a monohydric alcohol; and a glycol or glycol ether, wherein the ratio of monohydric alcohol:glycol or glycol ether by weight is from 3:1 to 1:1; and saccharine, wherein the ratio of nicotine or a pharmaceutically acceptable derivative or salt thereof:saccharine by weight is from 12:1 to 5.5:1, and wherein the composition is deliverable to a user using a simulated cigarette having a non-metered valve with an inhalable droplet diameter wherein at least 50 percent of the droplets have a diameter of 5 μm or less.

33. A simulated cigarette configured to provide a user thereof with a nicotine arterial $C_{max}$ of up to 15 ng/ml and/or with a $t_{max}$ of from 10 seconds to 20 minutes, comprising:
a housing;

a pressurised reservoir of inhalable composition within the housing; and an outlet for the inhalable composition from the reservoir and out of the housing, the outlet being configured to elect the inhalable composition therefrom in the form of droplets, at least 50 percent of the droplets have a diameter smaller than 5 μm, wherein the inhalable composition comprises:

nicotine or a pharmaceutically acceptable derivative or salt thereof;

at least 90% w/w of a propellant, wherein the propellant is a hydrofluorocarbon;

a monohydric alcohol; and 0.1 to 1% w/w of a glycol and/or glycol ether, wherein the glycol and/or glycol ether comprises propylene glycol, and wherein the ratio of monohydric alcohol: glycol or glycol ether by weight is from 3:1 to 1:1.

34. A method of treating nicotine addiction using the composition of claim 1.

35. The composition of claim 1, wherein the droplets have the following size profile:

Dv 90 of less than 5 μm, and/or

Dv 50 of less than 0.8 μm, and/or

Dv 10 of less than 0.3 μm.

36. The composition of claim 32, wherein the droplets have the following size profile:

Dv 90 of less than 5 μm, and/or

Dv 50 of less than 0.8 μm, and/or

Dv 10 of less than 0.3 μm.

* * * * *